(12) United States Patent
Kosecoff (10) Patent No.: US 12,311,040 B2
(45) Date of Patent: May 27, 2025

(54) PHOTONIC STRUCTURE FOR DYNAMIC EXPRESSION OF COLORS AND EFFECTS

(71) Applicant: L'Oreal, Paris (FR)

(72) Inventor: David B. Kosecoff, San Francisco, CA (US)

(73) Assignee: L'Oreal, Paris (FR)

( * ) Notice: Subject to any disclaimer, the term of this patent is extended or adjusted under 35 U.S.C. 154(b) by 288 days.

(21) Appl. No.: 17/363,821

(22) Filed: Jun. 30, 2021

(65) Prior Publication Data

US 2023/0000731 A1    Jan. 5, 2023

(51) Int. Cl.
| | |
|---|---|
| *A61K 8/02* | (2006.01) |
| *A61K 8/25* | (2006.01) |
| *A61K 8/29* | (2006.01) |
| *A61Q 1/02* | (2006.01) |
| *G06K 9/00* | (2022.01) |
| *G06V 40/16* | (2022.01) |

(52) U.S. Cl.
CPC .............. *A61K 8/0283* (2013.01); *A61K 8/25* (2013.01); *A61K 8/29* (2013.01); *A61Q 1/02* (2013.01); *G06V 40/166* (2022.01); *G06V 40/169* (2022.01); *A61K 2800/438* (2013.01); *A61K 2800/612* (2013.01); *A61K 2800/63* (2013.01); *A61K 2800/651* (2013.01); *A61K 2800/81* (2013.01)

(58) Field of Classification Search
CPC .......... A61K 8/0283; A61K 8/25; A61K 8/29; A61K 2800/438; A61K 2800/612; A61K 2800/63; A61K 2800/651; A61K 2800/81; G06V 40/169; G06V 40/166; A61Q 1/02
See application file for complete search history.

(56) References Cited

U.S. PATENT DOCUMENTS

| | | | | |
|---|---|---|---|---|
| 5,456,905 | A | * | 10/1995 | Valenty ................ B05D 7/532 522/89 |
| 8,110,281 | B2 | | 2/2012 | Downing |
| 8,252,209 | B2 | * | 8/2012 | Raymo ................ C07D 498/04 252/582 |
| 2005/0257335 | A1 | * | 11/2005 | Dumousseaux ......... A61Q 1/02 8/406 |
| 2010/0252061 | A1 | * | 10/2010 | Samain .................... A61K 8/69 132/200 |
| 2012/0017929 | A1 | | 1/2012 | Samain et al. |
| 2012/0024308 | A1 | | 2/2012 | Giron et al. |
| 2016/0316886 | A1 | * | 11/2016 | Samain ................ A45D 34/042 |

FOREIGN PATENT DOCUMENTS

| | | | | |
|---|---|---|---|---|
| CN | | 112208237 A | * | 1/2021 |
| FR | | 2 894 140 | | 6/2007 |
| JP | | 2007 055062 | | 3/2007 |
| JP | | 5 242709 | | 7/2013 |
| WO | WO 2009/016782 | | | 2/2009 |

OTHER PUBLICATIONS

English (Machine) translation of CN-112208237-A (Year: 2023).*
K. R. Phillips, G, T. England, S. Sunny, E. Shirman, T. Shirman, N. Vogelde, and J. Aizenberg. "A colloidoscope of colloid-based porous materials and their uses," Chem. Soc. Rev., 2016, 45, 281-322 (Year: 2016).*
Written Opinion of French Application No. FR2111031, mailed Oct. 18, 2021 (no English Translation available).
Notification of Search Report of French Application No. FR2111031, mailed Jun. 10, 2022 (no English Translation available).
Search Report of French Application No. FR2111031, mailed Jun. 3, 2022 (no English Translation available).
Jin et al., Photo-Chromeleon: Re-Programmable Multi-Color Textures using Photochromic Dyes, HCI Engineering, MIT C SAIL, 2019.

* cited by examiner

*Primary Examiner* — Michael P Cohen
(74) *Attorney, Agent, or Firm* — Christensen O'Connor Johnson Kindness PLLC

(57) ABSTRACT

Photochromic formulations including a core material and a photochromic layer overlying the core material and forming a particle are provided. The photochromic layer may include a plurality of photochromic materials, including a first photo-responsive pigment characterized by reversible diffuse reflectance at a first central wavelength from 490 nm to 520 nm in response to irradiation by photons of a first characteristic wavelength, a second photo-responsive pigment characterized by reversible diffuse reflectance at a second central wavelength from 570 nm to 590 nm in response to irradiation by photons of a second characteristic wavelength, and a third photo-responsive pigment characterized by reversible diffuse reflectance at a third central wavelength from 450 nm to 495 nm and a fourth central wavelength from 625 nm to 740 nm in response to irradiation by photons of a third characteristic wavelength. The first, second, and third characteristic wavelengths may be different.

18 Claims, 7 Drawing Sheets

PHOTONIC STRUCTURE FOR DYNAMIC EXPRESSION OF COLORS AND EFFECTS

SUMMARY

Methods, systems, and materials for integrated photochromic cosmetic application are described. A photochromic formulation may be or include a core material and a photochromic layer overlying the core material and forming a particle centered around the core material.

In some embodiments, the photochromic layer may be or include a plurality of photochromic materials, including a first photo-responsive pigment characterized by reversible diffuse reflectance at a first central wavelength from 490 nm to 520 nm in response to irradiation by photons of a first characteristic wavelength. The photochromic layer may include a second photo-responsive pigment characterized by reversible diffuse reflectance at a second central wavelength from 570 nm to 590 nm in response to irradiation by photons of a second characteristic wavelength. The photochromic layer may also include a third photo-responsive pigment characterized by reversible diffuse reflectance at a third central wavelength from 450 nm to 495 nm and a fourth central wavelength from 625 nm to 740 nm in response to irradiation by photons of a third characteristic wavelength. The first characteristic wavelength, the second characteristic wavelength, and the third characteristic wavelength may be the same or different.

In some embodiments, the first photo-responsive pigment may be or include 1,2-bis(2-methyl-5-phenyl-3-thienyl)-3,4,4,5,5-hexafluorocyclopentene. The second photo-responsive pigment may be or include 1,2-bis(2-methyl-5-phenyl-3-thienyl)-3,3,4,4,5,5-hexafluorocyclopentene. The third photo-responsive pigment may be or include 1,2-bis(3-methylbenzo(b)thiophen-2-yl)perfluorocyclopentene. The photochromic layer may be or include spiropyrans, spirooxazines, diarylethenes, azobenzenes, quinones, silver halides, or zinc halides. The photochromic layer may be or include DAE-0001, DAE-0012, and DAE-0068.

In some embodiments, the core material may be or include a reflective mineral. The reflective mineral may be or include mica, titanium oxide, or silicon oxide. The photochromic formulation may further include a shimmer-control layer, interposed between the core material and the photochromic layer, wherein the shimmer-control layer includes a photo-responsive material characterized by a transition from visible transparency to visible opacity when exposed to irradiation of a characteristic wavelength, the visible opacity corresponding to broad reflectance in the visible spectrum. The transition from visible transparency to visible opacity may be progressive in proportion to an extent of the irradiation. The particle may be characterized by a diameter less than or equal to 20 micrometers.

A photochromic formulation may be or include a core material and a structural color material overlying the core material forming a particle centered around the core material.

In some embodiments, the structural color material may be or include a photonic crystal material. The photonic crystal material may be or include a first photonic crystal material characterized by a first structural color in the blueish range. The photonic crystal material may be or include a second photonic crystal material characterized by a second structural color in the greenish range. The photonic crystal material may be or include a third photonic crystal material characterized by a third structural color in the reddish range. The photochromic formulation may further include a plurality of particles including the particle. The plurality of particles may include a first proportion of particles comprising the first nanostructured material. The plurality of particles may include a second proportion of particles comprising the second nanostructured material. The plurality of particles may also include a third proportion of particles comprising the third nanostructured material. The first proportion, the second proportion, and the third proportion may be substantially equal or disparate.

In some embodiments, the structural color material may further include a photo-responsive matrix characterized by a transition from visible transparency to visible opacity when exposed to irradiation of a characteristic wavelength associated with the respective structural color. The nanostructured material may be or include a plurality of porous clusters suspended in the photo-responsive matrix. The porous clusters may be or include inverse opal formed from silicon oxide or titanium oxide. The photochromic formulation may further include a brightness layer overlying the photochromic layer. The brightness layer include a photo-responsive material characterized by a transition from visible transparency to visible opacity when exposed to irradiation of a characteristic wavelength, the visible opacity corresponding to broad absorptance in the visible spectrum. The transition from visible transparency to visible opacity may be progressive in proportion to an extent of the irradiation. The brightness layer may be or include spiropyran or naphthopyran. The core material and the structural color material may be the same material or different materials.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The foregoing aspects and many of the attendant advantages of the present disclosure will become more readily appreciated as the same become better understood by reference to the following detailed description, when taken in conjunction with the accompanying drawings.

In the above-referenced drawings, like reference numerals refer to like parts throughout the various views unless otherwise specified. Not all instances of an element are necessarily labeled to simplify the drawings where appropriate. The drawings are not necessarily to scale, emphasis instead being placed upon illustrating the principles being described.

DETAILED DESCRIPTION

Application of cosmetics and makeup in patterns and shapes can be difficult by hand. For example, intricate designs and theatrical makeup are typically applied by certified makeup professionals. Additionally, self-application can be a challenge generally for those with limited mobility. Currently, solutions are being explored through the development of handheld tools, such as cartridge-plus-dispenser solutions, which implement light-activated cosmetics guided by hand. Despite representing a technological alternative to brushes, such tools are limited by cartridge sizes, cleaning methods, inability to mix or blend colors, short battery life, and lack of location awareness. Also, by depending on a handheld device, such tools do not address accessibility concerns.

Photochromic formulations are described for applying a cosmetic design on a body surface, such as a subject's face or other region of interest, using one or more illumination sources. Described embodiments use photo-responsive materials in combination with reflective and/or structural color materials to define one or more exposure patterns mapped to the body surface using a projection of the cosmetic design onto a 3D mapping of the body surface. Described embodiments are useful in many contexts, including cosmetics or body art applications, skin feature mapping or monitoring, dermatological diagnosis or treatments, or telehealth applications. In the context of such applications, described embodiments provide precision and greater ease of use over complex manual routines.

In described embodiments, a photochromic formulation may include a micrometer-scale particulate material including multiple layers. Each layer may individually modulate a color or a cosmetic effect, including but not limited to shimmer, shine, brightness, angular color, luminescence, iridescence, or fluorescence. The layers may each be actuated/modulated/addressed by one or more wavelengths, as part of applying the cosmetic design both in terms of color fidelity and cosmetic effects. In an illustrative example, a micrometer-scale particle of the photochromic formulation may include a reflective core including mica or titania, a shimmer-control layer that includes a photo-responsive material that transitions from transparency to opacity under a specific wavelength, and a color layer including four photochromic materials. The photochromic materials may be individually addressable by four different and distinct wavelengths. In this way, a region of the body surface can be exposed with a combination of the four wavelengths to express a unique color, for example, as is used in CMYK pigment systems. By applying the photochromic formulation onto the body surface, for example, as a face powder or cream, exposure of the body surface (and thus the photochromic formulation) to an illumination source according to an exposure pattern can transfer the design in a touch-free manner.

Without being limited to a specific system or method, systems and methods for applying such cosmetic designs are also described in the context of a sensor-bearing system. Sensors suitable for use in described embodiments include 2-dimensional (2D) or 3-dimensional (3D) cameras, proximity sensors, or other integrated or peripheral cameras or sensors. Depth sensors are used in some embodiments to obtain 3D information about surfaces and include a range of possible hardware suitable for this purpose, including RGB or infrared stereoscopic cameras, laser or infrared LiDAR sensors, and dot projectors. 3D scans enable improved measurement of actual dimensions of a body surface and allow depth sensing, which can help to determine, for example, how far the body surface is from the camera, or detailed information about particular skin features, such as wrinkles. Reference points obtained through high-quality 3D scanning in accordance with described embodiments provides greater accuracy for determining location than traditional reference points obtained with 2D imaging, such as eyes, lips, noses, or other prominent facial features, and are particularly helpful where the region of interest is occluded.

The systems described expose the surface with multiple actuating wavelengths in accordance with the cosmetic design as mapped onto the 3D information collected by the sensors. In this way, the photochromic formulation, applied to a region of the body surface, can be made to take on the cosmetic design accurately and precisely by illumination with the actuating wavelengths rather than manual application of cosmetics. Advantageously, the materials, systems, and methods described also provide improved accessibility to users with limited mobility or dexterity, for whom cosmetic application, such as makeup, may otherwise involve assistance by another person. As an additional advantage, the materials, systems, and methods described also permit a user to develop, try, or experiment with multiple cosmetic designs without removing or changing the photochromic formulation. For example, in some embodiments, the photochromic formulation can be reset using the same actuating wavelengths used to apply the design, thereby permitting another cosmetic design to be applied. Such versatility reduces the number of materials and layers applied for each design, and further simplifies cosmetic application.

Figure 1:
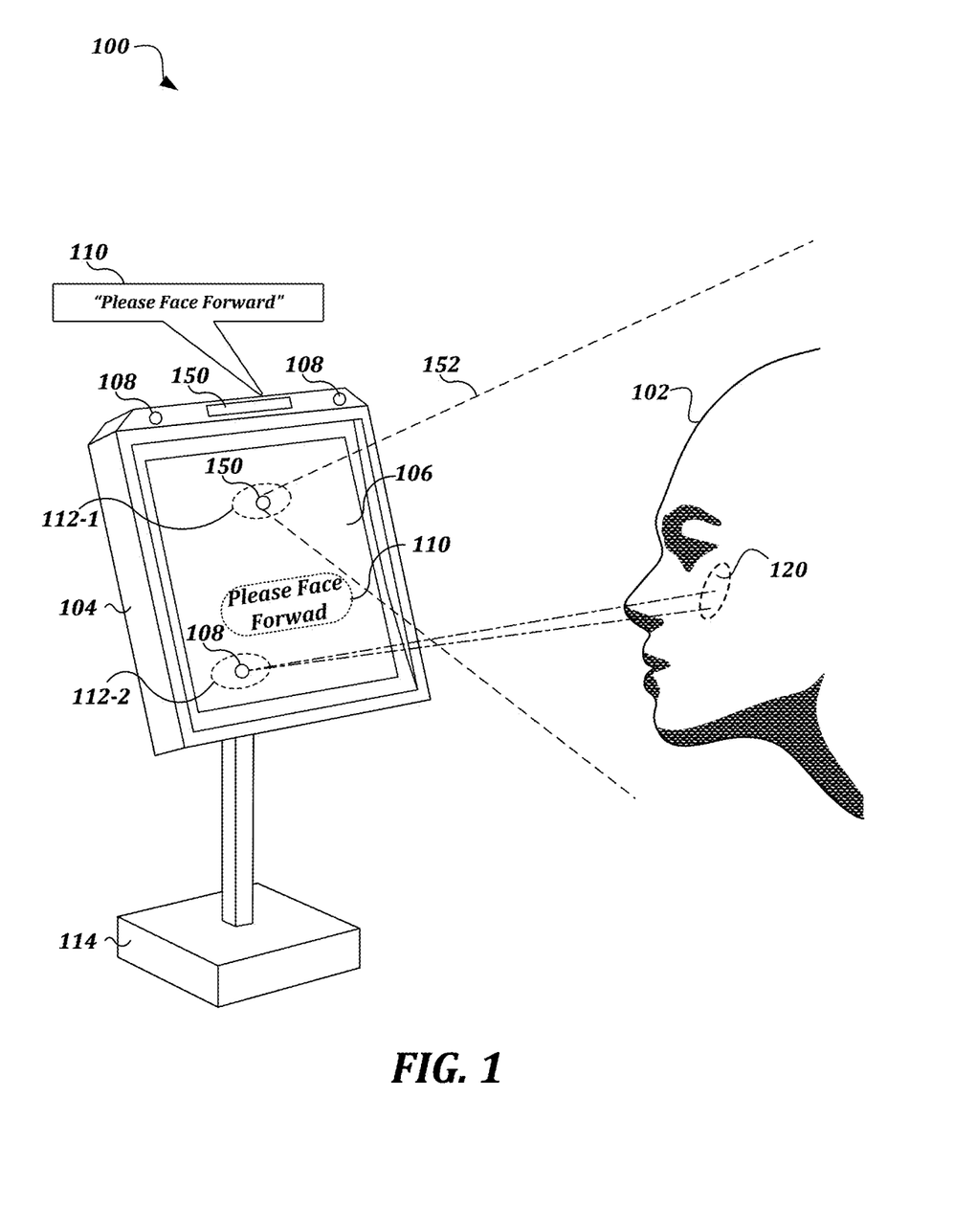
FIG. 1 is a schematic illustration of an embodiment of a system incorporating sensors and an illumination source for application of cosmetic designs, in accordance with various embodiments.

FIG. 1 is a schematic illustration of an example system 100 incorporating sensors and an illumination source for application of cosmetic designs, according to various embodiments. While the embodiments of the photochromic material described in reference to the forthcoming figures are illustrated in the context of example system 100, alternative approaches are also contemplated. The system 100 is not intended as the sole system for use with the photochromic materials described below.

As part of the example system 100, one or more cameras 150 of a client computing device 104 includes one or more cameras and captures images of a subject's face 102. In the example shown, the client computing device 104 is a purpose-built mobile computing device including a visible light mirror 106, one or more illumination sources 108, and one or more user interface elements 110 to prompt the subject with visual and/or auditory prompts. For example, the interface elements 110 may be or include a display electronically coupled with the computer system to generate a visual prompt (e.g., "please face forward") either in a peripheral physically coupled with the mirror 106. Additionally or alternatively, the client computing device 104 may be electronically coupled with an acoustic speaker to generate an auditory prompt.

The mirror 106 may include one or more portions 112 characterized by unidirectional transparency, for example, in ultraviolet, visible, and/or infrared spectral ranges. The camera(s) 150 may be optically coupled with the visible light mirror 106 to receive visible light via a first portion 112-1, and the illumination source(s) 108 may be optically coupled with the visible light mirror 106 and configured to emit a plurality of discrete wavelength channels via a second portion 112-2 of the mirror 106. In this way, the mirror 106 may appear uniform, and the system 100 may appear aesthetically as an ordinary cosmetic mirror without outward indication that the system 100 incorporates electronics, cameras 150, or illumination sources 108. For example, the components of the client computing device 104 may be integrated into a housing 114 that appears similar to a consumer cosmetic mirror rather than an electronics system. In this example, the housing 114 may conceal power sources, heat management systems, and other components.

While the client computing device 104 is illustrated in a particular configuration (e.g., as a countertop mirror or vanity mirror), additional and/or alternative form factors are contemplated. For example, the system 100 may include a smartphone or tablet computer in communication with the client computing device 104, such that one or more computer-executable operations are undertaken by the smartphone or tablet computer rather than by the client computing device 104. In this way, the client computing device 104 may be or include smaller housings 114, including, but not limited to, a cosmetics compact or an electronic peripheral configured to electronically couple with a smartphone or tablet computer that includes the camera 150, the illumination source 108, or both. Similarly, the mirror 106 can be or include a full-size wall mirror, such that the client computing device 104, the camera(s) 150 and the illumination source(s) 108 may be positioned behind the mirror 106 and the one or more portions 112 may be located relative to the camera(s) 150 and the illumination source(s) 108. In such a configuration, the system 100 may be installed as a fixture, rather than as a portable system and a single mirror 106 may be configured to conceal multiple client computing devices 104, multiple cameras 150, and multiple illumination sources 108, corresponding to a number of "makeup stations," as in a salon or makeup trailer.

The illumination source 108 may include one or more optics configured to form a beam and to scan the beam. The optics may include lenses or mirrors internal to the housing 114 that may be actuated or otherwise controlled to direct a beam from the illumination source(s) 108 to the subject's face 102. For example, the illumination source 108 may be or include one or more laser sources corresponding to the plurality of discrete wavelength channels, as described in more detail in reference to FIG. 4B, below. In some embodiments, the illumination source 108 includes multiple light-emitting diodes corresponding to the plurality of discrete wavelength channels. Similarly, the illumination source may be or include a continuous source (e.g., a tungsten halide or broad-spectrum source) and a plurality of bandpass filters to generate the discrete wavelength channels used by the system 100 to apply a cosmetic design.

The client computing device 104 may be in electronic communication with additional systems via a network or over near-field communication protocols (e.g., wifi, bluetooth, etc.). For example, the client computing device 104 may pair with a mobile electronic device, such as a smart phone or tablet, from which the client computing device 104 may receive an identifier of a design. Similarly, the client computing device 104 may communicate with a server, storing numerical representations of designs, and may access the design from the server. The server may be a remote server or may be a local server, where the terms "remote" and "local" are used both to refer to physical proximity to the system 100 and to denote whether the client computing device 104 and the server are configured to communicate over a public network, such as the internet, or a distributed network system (e.g., a cloud system). In some cases, the client computing device 104 may store design data locally for a number of cosmetic designs, for example, using a non-transitory computer readable storage medium (e.g., SSD flash memory, hard disk drives, etc.). For example, the client computing device 104 may receive newly released cosmetic design data and associated metadata from the server, such as identifier information and interface data (e.g., images representing the cosmetic design on a model), which may be provided via the interface elements 110 or via the mobile electronic device. In such cases, the system may be configured to operate with intermittent or no network connectivity.

In some embodiments, the camera 150 acts as a far-field camera positioned and configured to capture video or still images of subject's face 102, as well a region of interest 120 of the subject's face 102, such that the region of interest 120 is within the field of view 152 of the camera(s) 150. In the example shown, the region of interest 120 is shown as a portion of the left cheek of the subject's face 102, but the region of interest 120 may cover a larger portion of the subject's face 102, such as the entirety of the subject's face 102. In some embodiments, the camera unit 150 includes more than one camera, such as for stereoscopic image or video capture and/or depth sensing. In some embodiments, the camera unit 150 also includes one or more sensors other than cameras (e.g., a LiDAR sensor or infrared dot projector for depth sensing, a proximity sensor for proximity detection, etc.). In some embodiments, an infrared dot projector projects infrared dots onto a surface, and reflections from the surface are measured by an infrared camera to determine the distance each dot is from the projector system. When working in conjunction with a 3D camera, these depth measurements can be mapped onto a captured 3D image. This approach is used in some embodiments to generate a 3D model of a body surface, and for real-time tracking of additional features to be used for mapping a cosmetic design onto the subject's face 102 or other body parts.

Figure 2A:
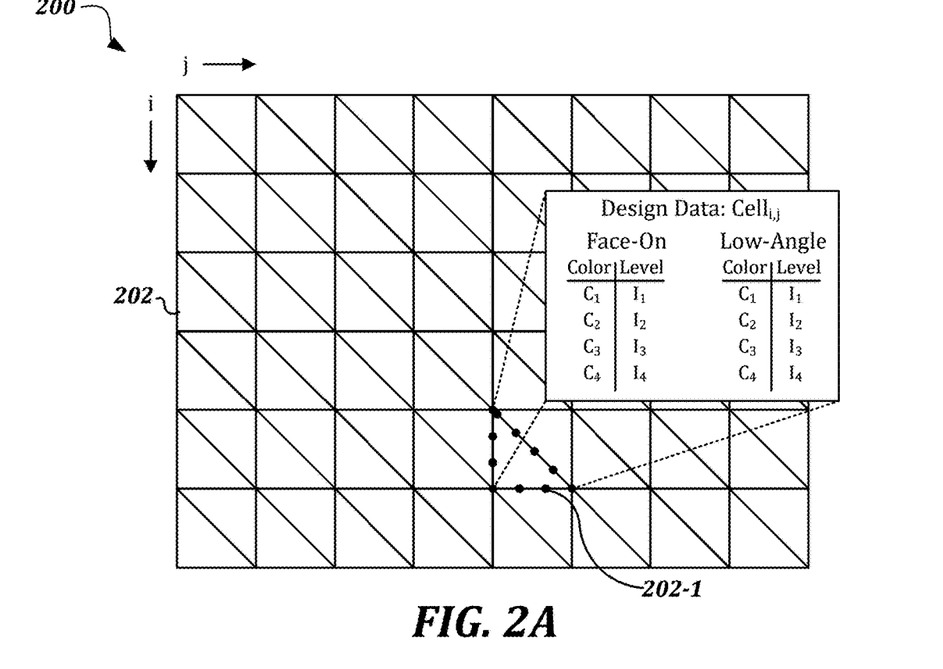
FIG. 2A is a schematic illustration of a numerical representation of a cosmetic design as a polygonal mesh including a tensor of design data in a face-on direction and a low-angle direction, in accordance with various embodiments.

FIG. 2A is a schematic illustration of a numerical representation of an example cosmetic design 200 as a polygonal mesh including a tensor of design data in an face-on direction and a low-angle direction, according to various aspects of the present disclosure. The design 200 represents an exemplary visualization of a cosmetic design, including multiple polygons 202, where each polygon 202 represents a unit of the numerical representation, akin to a pixel in a digital image. Where the system implementing the processes described herein (e.g., system 100 of FIG. 1) may project the design 200 onto a surface mapping of a user's face (e.g., subject's face 102 of FIG. 1), the polygons 202 may be or include triangles or other shapes that provide greater flexibility for projection and surface mapping relative to square or rectangular pixels.

As shown, a first polygon 202-1 of the design 200, referenced as $Cell_{i,j}$ in the i-j plane of the numerical representation, may include multiple types of design data corresponding to different layers of the design 200. For example, the design data for the first polygon 202-1 may include, but is not limited to, a face-on color tuple and a low-angle color tuple, indicating two different colors to be generated by the system 100 at different angles. Each tuple may include color level information corresponding to the photo-responsive materials incorporated into a photochromic formulation. For example, the photochromic formulation may include one, two, three, four, five, or more different photo-responsive materials.

By selectively modulating the photo-responsive materials in accordance with the color levels for each polygon, the cosmetic design 200 may be applied to the user. As described in more detail in reference to FIG. 5, angle-dependent color may be provided using angled illumination, such that a cosmetic design may include iridescence or other angular color effects. While each polygon 202 is illustrated as having a uniform characteristic size, it is to be understood that the polygons are representative of a tensor of color data that is referenced by cell entries in i-j space, rather than in cartesian coordinates. In this way, the first polygon 202-1 may be larger or smaller than neighboring polygons 202 when projected into a physical dimension, such as when applied to a facial mapping of a user for application of the cosmetic design 200 (e.g., region of interest 120 of the subject's face 102 of FIG. 1).

Figure 2B:
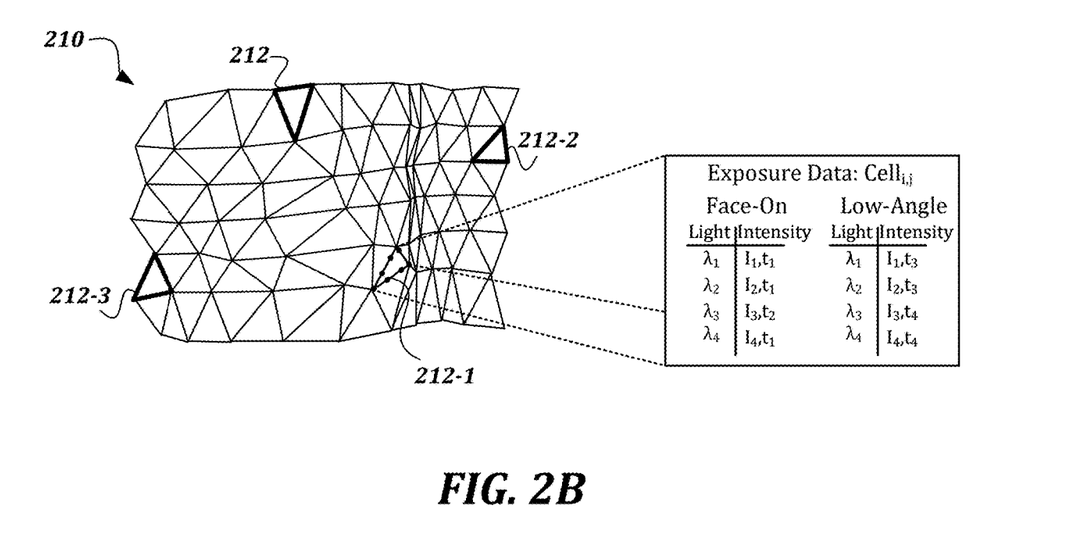
FIG. 2B is a schematic illustration of a 3-dimensional model projection of the cosmetic design onto a face mapping collected using the system of FIG. 1, in accordance with various embodiments.

FIG. 2B is a schematic illustration of an example 3-dimensional projection 210 of the cosmetic design 200 onto a face mapping collected using the system of FIG. 1, according to various embodiments. As described in more detail in reference to FIG. 1, the system 100 is configured to receive the cosmetic design 200 and to generate an exposure pattern. As part of the operations of the system 100, the cosmetic design 200 may be projected onto a 3D mapping of the portion of the user's body (e.g., subject's face 102 of FIG. 1), The 3D model includes several reference points 212 in the form of corresponding triangles (although other polygon shapes are also contemplated) of a mesh structure.

Generating the 3D projection 210 may include multiple computational operations to generate a numerical representation of a portion of a face of the user using the camera (e.g., a facial mapping). The camera may be or include multiple image sensors configured to capture stereoscopic images. In this way, the numerical representation of the portion of the face may be or include a tensor of position information defining a surface of the face (e.g., in the region of interest 120 of FIG. 1). Examples of computational techniques include edge-detection, feature or point detection and tracking, and/or point-cloud methods. For example, the system 100 may be configured with a time-of-flight camera, with LiDAR systems, or with stereoscopic cameras, such that the facial mapping may represent a surface generated by contours connecting points and/or features. In some embodiments, the system 100 may include an implementation of machine learning, such as a face detection/mapping module, that may be trained to predict the facial mapping based on a subset of features and/or points measured by the camera. In this way, the system 100 may be configured to reduce the number of measurements used to generate the mapping, which may improve system performance, for example, by reducing the length of time used to capture images of the user's face.

Other adaptations can be performed for variations in lighting conditions, viewing angles, or other factors. As one example, a light sensor mounted on the client computing device 104 can be used to measure current lighting conditions relative to a baseline lighting condition. If the environment is too bright or too dark, the client computing device 104 may generate a prompt to increase illumination and/or may activate an illumination source (e.g., illumination source 108 of FIG. 1) that may or may not be visible to the subject (e.g., an infrared source to provide invisible illumination). In some embodiments, the client computing device 104 may provide feedback to a user (e.g., via synthesized voice cues or visual indications) to adjust the lighting conditions for better results. In some embodiments, the system may generate feedback to instruct the user to reposition relative to the camera(s) (e.g., generating a prompt to reposition the user's face from a face-on to a side-on position). It should be understood that described embodiments are capable of implementation in many possible ways to determine matches between captured image data and texture data in a 3D model, including matching detected edges or contours, color/pixel values, depth information, or the like in different combinations, and at particular threshold levels of confidence, any of which may be adjusted based on lighting conditions, user preferences, system design constraints, or other factors.

The projection 210 may be generated by various means to reduce artifacts of the projection onto the face. For example, the polygons into which the design 200 is divided may be heterogeneously scaled, skewed, or otherwise modified when generating the projection 210, as illustrated. For example, where the cosmetic design may include each polygon with a uniform size, the projection 210 may include many different sizes for the polygons 212. In some embodiments, resizing may correspond to the contours of the facial mapping, where regions of high dynamic range correspond to smaller polygons 212 and regions of low dynamic range correspond to larger polygons 212. Additionally and/or alternatively, the projection 210 may be resized in accordance with information density. For example, where the number of polygons 202 making up the design 200 correspond to the resolution of the design, analogous to a pixel resolution of a digital image, information-rich regions of the design 200 may include relatively high numbers of polygons 202, compared to regions that include negligible design information. As an illustrative example, more polygons may be used to describe the regions around facial features, such as eyes, nose, mouth, or eyebrows, in contrast to regions of the cheeks, jaw, forehead, etc. In this way, the projection 210 may be include exposure data for both a face-on direction (e.g., substantially normal to the surface) and for a low-angle direction, as defined for one or more angles of the user's face relative to the illumination source. In this context, "substantially" refers to a range of ±20% of the stated value.

The exposure data illustrated in FIG. 2B may be generated by taking into account the intensity values of each color channel included in the design 200, as well as exposure data for the photo-responsive materials. For example, color mixing for a first polygon 212-1, as indicated by the intensity data of the design 200, may be effected by exposing the first polygon to the multiple distinct wavelength channels (e.g., $\lambda_{1-4}$) for different durations corresponding to the characteristic activation/deactivation time of the different dies. The physical mechanisms of photochromic materials are dynamic and sometimes may include reversible activation/ deactivation, such that multiple designs 200 may be applied using a single application of photo-responsive material. In some embodiments, a "wipe" operation may be implemented by exposing the die to a neutralization wavelength.

The projection 210 may reduce artifacts of applying the design to the face. For example, the polygons into which the design 200 is divided may be heterogeneously scaled, skewed, or otherwise modified when generating the projection 210, as illustrated. For example, where the cosmetic design may be described with each polygon having a uniform size, the projection 210 may include many different sizes for the polygons 212. In some embodiments, resizing may correspond to the contours of the facial mapping, where regions of high dynamic range correspond to smaller polygons 212 and regions of low dynamic range correspond to larger polygons 212. Additionally and/or alternatively, the projection 210 may be resized in accordance with information density. For example, where the number of polygons 202 making up the design 200 correspond to the resolution of the design, analogous to a pixel resolution of a digital image, information-rich regions of the design 200 may include relatively high numbers of polygons 202, compared to regions that include negligible design information. As an illustrative example, more polygons may be used to describe the regions around facial features, such as eyes, nose, mouth, or eyebrows, in contrast to regions of the cheeks, jaw, forehead, etc. In this way, the projection 210 may include exposure data for both a face-on direction (e.g., substantially normal to the surface) and for a low-angle direction, as defined for one or more angles of the user's face relative to the illumination source, using a dynamic mesh accounting for surface features.

Figure 3:
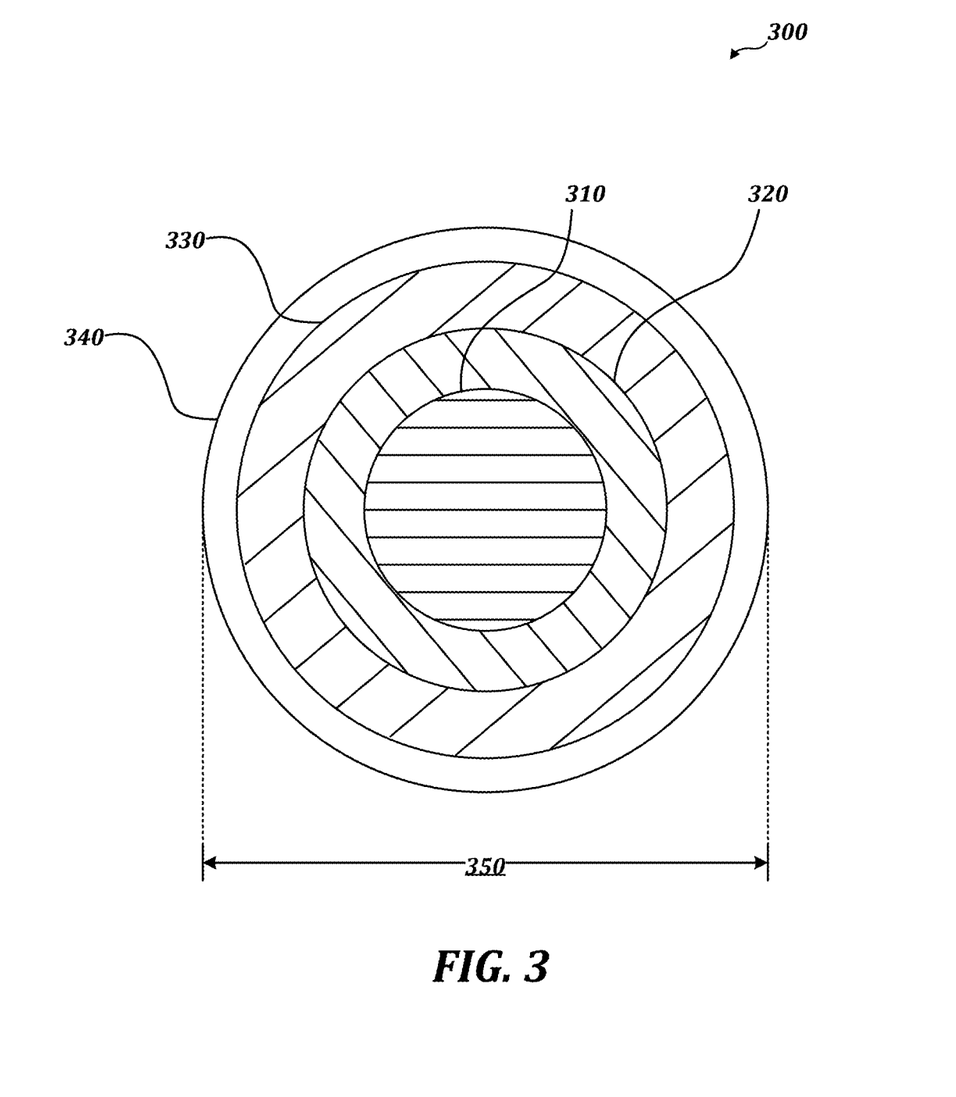
FIG. 3 is a schematic illustration of a photochromic formulation including a core-shell structure, in accordance with various embodiments.

FIG. 3 is a schematic illustration of an example photochromic formulation 300 including a core-shell structure, in accordance with various embodiments. The example photochromic formulation 300 includes multiple layers to facilitate individual modulation/actuation of different elements of a cosmetic design (e.g., cosmetic design 200 of FIG. 2A). A core material 310 may form the center of a particle, around which may be disposed a number of layers. The example photochromic formulation 300 is illustrated as a number of concentric layers for simplicity of illustration, although it is understood that the layers may include surface structuring resulting from the morphology of the layers and/or the methods applied to synthesize the materials. Surrounding the core material 310, the example photochromic formulation 300 may include a photochromic layer 330. In some embodiments, a shimmer control layer 320 may be interposed between the core material 310 and the photochromic layer 330. Similarly, an encapsulation layer 340 may be disposed overlying the photochromic layer 330. In some embodiments, the particle may be characterized by a characteristic dimension, such as a diameter 350.

The core material 310 may be or include a reflective mineral. In some embodiments, the reflective mineral may be or include mica, titanium oxide, or silicon oxide. In this way, the core material 310 may impart shimmer, may amplify the color effect of the photochromic formulation 300, and may impart specular color to the photochromic formulation 300. In some embodiments, the core material 310 may be or include a material that fluoresces under ambient conditions (e.g., Sun, UV, etc.), for example, titanium oxide nanoparticles. In this way, the core material 310 may provide a white foundation to improve color fidelity of the photochromic layer 330. Similarly, the core material 310 may be or include a polymeric material characterized by a diffuse color, which may be selected from a range of shades or tones. In an illustrative example, the core material 310 includes a mixture of titanium oxide nanoparticles suspended in a white polymer microbead with a diameter from 0.1-5 µm, or larger. In this example, the core material 310 can provide a diffuse white foundation for the photochromic layer 330 under indoor conditions, and a brilliant white foundation under sunlit conditions that will amplify the perceived intensity of the photochromic layer. Advantageously, such an approach permits the photochromic formulation 300 to respond to changing ambient conditions by amplifying or damping the brightness of the color.

The shimmer control layer 320, interposed between the core material 310 and the photochromic layer 330, may be or include a photo-responsive material characterized by a transition from visible transparency to visible opacity when exposed to irradiation of a characteristic wavelength. The visible opacity may correspond to broad reflectance in the visible spectrum. Additionally or alternatively, the visible opacity may correspond to a solid diffuse color. In this way, the shimmer control layer 320 may permit modulation of any optical properties of the core material 310 independently of the photochromic layer 330. In some embodiments, the transition from visible transparency to visible opacity is progressive in proportion to an extent of the irradiation. For example, the shimmer control layer may be or include a photo-responsive polymer, including but not limited to spiropyran, sprooxazine, diarylethenes, or naphthopyran, that transitions either physical confirmation or electronic state in response to irradiation at the characteristic wavelength. As an illustrative example, spiropyran transitions under UV irradiation to absorb photons of visible light, and therefore appear colorful. When the UV source is removed, the molecules gradually relax to their ground state. Without being limited to a particular range, the characteristic wavelength may be in the UV range, such as about 400 nm or less, about 380 nm or less, about 360 nm or less, about 340 nm or less, about 320 nm or less, within the ranges of energy that human skin is adapted to absorb at least in intermittent exposure (e.g., UV-A and/or UVB). In some embodiments, the characteristic wavelength may be in the visible range, from about 380 nm to 750 nm, such that the shimmer-control layer may be modulated between a UV-absorber and a visible-absorber under irradiation by visible light, which may be preferred over UV light for some users. For example, some diarylethene coordination complexes, such as polyoxometalate diarylethene coordination complexes, switch between UV-absorbers to broad-spectrum absorbers from about 425 nm to about 800 nm, centered around a wavelength of about 620 nm after irradiation at a characteristic wavelength of 400 nm. In this context, the term "about" is used to indicate a margin of ±5% on either side of the stated value.

The photochromic layer 330 may be or include multiple photochromic materials. The photochromic materials may be or include materials selected to provide a color-rendering dyad, triad, tetrad, or larger number of materials, with which a range of colors represented in the cosmetic design (e.g., cosmetic design 200 of FIG. 2) may be rendered with acceptable fidelity to satisfy the aesthetic sense of the user. In some embodiments, the photochromic layer includes three photochromic materials to render a cyan-magenta-yellow triad (CMY). In some embodiments, each of the three photochromic materials are individually modulated by a respective characteristic wavelength, where a first characteristic wavelength, a second characteristic wavelength, and a third characteristic wavelength are different wavelengths.

To reduce cross-talk between color channels in the photochromic layer, the three characteristic wavelengths may be provided by an illumination source (e.g., illumination source(s) 108 of FIG. 1) with three distinct wavelength channels, such as line sources or filtered light sources (e.g., an RGB projector).

For example, a first photo-responsive dye or pigment may be included that is characterized by reversible diffuse reflectance at a first central wavelength from 490 nm to 520 nm in response to irradiation by photons of a first characteristic wavelength. In this way, the first central wavelength may correspond to the cyan portion of the CMY triad. In some embodiments, the first characteristic wavelength may be an activation wavelength or a deactivation wavelength, such that the first photo-responsive dye or pigment may exhibit stable transparency that is modulated to a stable diffuse color in response to irradiation at the first characteristic wavelength. Alternatively, the first photo-responsive dye or pigment may exhibit stable diffuse color that is modulated to a stable transparency in response to irradiation at the first characteristic wavelength. For example, for deactivation mechanisms, the first characteristic wavelength may be from about 625 nm to about 740 nm, corresponding to red light. For activation mechanisms, the first characteristic wavelength may be generally in the ultraviolet range, as described above. In this context, the term "about" is used to indicate a margin of ±5% on either side of the stated value.

Similarly, a second photo-responsive dye or pigment may be characterized by reversible diffuse reflectance at a second central wavelength from 570 nm to 590 nm in response to irradiation by photons of a second characteristic wavelength. In this way, the second central wavelength may correspond to the yellow portion of the CMY triad. As described in reference to the first photo-responsive dye or pigment, the second photo-responsive dye or pigment may be modulated by an activation or deactivation mechanism. For deactivation mechanisms, the second characteristic wavelength be from about 450 nm to about 495 nm, corresponding to blue light. For activation mechanisms, the second characteristic wavelength may be generally in the ultraviolet range, as described above. In this context, the term "about" is used to indicate a margin of ±5% on either side of the stated value.

Similarly, a third photo-responsive dye or pigment may be characterized by reversible diffuse reflectance at a third central wavelength from 450 nm to 495 nm and a fourth central wavelength from 625 nm to 740 nm in response to irradiation by photons of a third characteristic wavelength. In this way, the third photo-responsive dye or pigment may correspond to the magenta portion of the CMY triad. As described in reference to the first photo-responsive dye or pigment, the third photo-responsive dye or pigment may be modulated by an activation or deactivation mechanism. For deactivation mechanisms, the second characteristic wavelength may be from about 495 nm to about 570 nm, corresponding to green light. For activation mechanisms, the second characteristic wavelength may be generally in the ultraviolet range, as described above. In this context, the term "about" is used to indicate a margin of ±5% on either side of the stated value. In some embodiments, the third photo-responsive dye or pigment may be or include more than one type of photo-responsive molecule to impart the third central wavelength and the fourth central wavelength rather than a single molecular structure imparting both.

In some embodiments, the photochromic layer 330 may be or include, but is not limited to, photochromic materials such as spiropyrans, spirooxazines, diarylethenes, azobenzenes, quinones, silver halides, or zinc halides. For example, the first photo-responsive pigment may be or include 1,2-bis(2-methyl-5-phenyl-3-thienyl)-3,3,4,4,5,5-hexafluorocyclopentene. The second photo-responsive pigment may be or include 1,2-bis(2-methyl-5-phenyl-3-thienyl)-3,3,4,4,5,5-hexafluorocyclopentene. The the third photo-responsive pigment may be or include 1,2-bis(3-methylbenzo(b)thiophen-2-yl)perfluorocyclopentene. In some embodiments, the photochromic layer may be or include a mixture of materials described by trade name. For example, in reference to the DAE naming system developed by Yamada Chemical Company, LTD. Of Japan, the photochromic layer may be or include DAE-0001, DAE-0012, and DAE-0068 photochromic dyes. Other DAE dyes or pigments may be available, including but not limited to DAE-0002, DAE-0003, DAE-0004, DAE-0005, DAE-0015, DAE-0016, DAE-0017, DAE-0018, DAE-0019, DAE-0020, or other functional photochromic dyes or pigments classified as "p-type" that isomerize in response to irradiation.

In some embodiments, the photochromic layer 330 may also include a fourth photochromic material to impart a black-channel as part of a CMYK tetrad (also referred to as the "key" channel). Similar to the photochromic materials described above, the fourth photochromic material may be characterized by a transition from visible transparency to visible opacity when exposed to irradiation of a characteristic wavelength (e.g., UV photons). In contrast to the CMY triad materials, the K material may be isomerized between a broad absorber (e.g., a diffuse black color) across the visible spectrum and a broad transmitter (e.g., transparent). The inclusion of the fourth photochromic material to impart the K-channel in the photochromic layer 330 provides improved color rendering fidelity to the photochromic formulation, as is observed in CMYK printing systems.

Additionally or alternatively, the photochromic layer 330 may be or include a material that exhibits structural color. In contrast to pigments and dyes, structural color is generated by interference effects caused by the structure of the material, rather than photon-absorption by electrons in atomic or molecular orbitals. In multilayer thin-film materials, for example, structural color can result from wavelength-dependent phase shifting that produces interference in a characteristic pattern in the visible spectrum, observed as a color. In contrast to photochromic materials described above, however, structural color may be fixed, rather than transitioning between two color states.

In this way, the photochromic layer 330 may be a structural color layer, including one of three or more structural color materials. In contrast to the photochromic pigments or dyes described above that render colors by subtractive color mixing, structural color is typically not susceptible to modulation by an activation/deactivation wavelength. Instead, materials exhibiting structural color are typically characterized by a static wavelength-dependent color, that manifests in response to exposure to photons at a characteristic wavelength, polarity, or other property. In this way, structural color materials may be selected to reproduce an additive color triad. Examples of an additive color triad include but are not limited to an "RGB" triad as in addressable pixel displays. In this way, the photochromic formulation 300 may include a mixture of particles including particles with different structural color materials, the proportion of which can be selected to produce different color rendering capabilities. In an illustrative example, the photochromic formulation can include a mixture of red-structural color particles, green-structural color particles, and blue-structural color particles, in substantially equal proportions (e.g., 1:1:1—R:G:B). In this context, "substantially" is used to indicate a distribution of values ±10% of the stated value.

In some embodiments, the structural color is imparted to the photochromic layer 330 by a nanostructured or microstructured material. For example, the structural color layer may be or include porous clusters suspended in a photo-responsive matrix. The porous clusters may be or include inverse opal, as may be formed from silicon oxide or titanium oxide. Inverse opals are three-dimensionally ordered macroporous photonic crystal particles, characterized by structural color that is tunable by synthesis parameters. For example, by synthesis of silicon oxide crystals in a colloidal matrix template that forms the photonic crystal structure after pyrolysis. As a photonic crystal material, a powder of the material can retain the structural color properties of the bulk crystal. In this way, a suspension of porous clusters that act as photonic crystals may be incorporated into a photochromic material that acts as the photo-responsive matrix. As such, the structural color layer may be provided by the core material 310, where the core material includes a photonic crystal characterized by a structural color.

In turn, the photo-responsive matrix modulates the exposure of the porous clusters to incident photons by transitioning from transparent to opaque under irradiation by a characteristic actuation/modulation wavelength. Similar to the photochromic materials described above, the photo-responsive matrix may be characterized by a transition from visible transparency to visible opacity, or the reverse, when exposed to irradiation of a characteristic wavelength (e.g., UV photons, visible photons, or infrared photons). As with the K-channel material or the shimmer control layer 320, the photo-responsive matrix material may be isomerized between a broad absorber (e.g., a diffuse black color), a broad reflector (e.g., a diffuse white color), or a narrow reflector (e.g., a specific diffuse color) to a broad transmitter (e.g., transparent). The specific diffuse color may be used, for example, to provide a neutral tone that may be matched to the skin tone, while black or white matrix materials may be used to provide foundations to promote color rendering fidelity. In some embodiments, the specific diffuse color may be provided by blending multiple photochromic materials in the photo-responsive matrix, such that the characteristic wavelength may include multiple wavelengths that together modulate the blend.

In terms of the structures illustrated in FIG. 3, the photochromic layer 330, as a structural color layer, may include a first photonic crystal material characterized by a first structural color in the blue range. The structural color layer, may include a second photonic crystal material characterized by a second structural color in the green range. The structural color layer, may include a third photonic crystal material characterized by a third structural color in the red range. In contrast to the photochromic materials, the structural color layer may be limited to a single structural color rather than a blend of all three. In this way, three color channels may be independently modulated by providing the three different photo-responsive matrix materials to the three photonic crystal materials, each selected to isomerize in response to irradiation by a different respective wavelength. As described in more detail in reference to FIG. 4B, a blend of three different structural color materials, incorporating three different photo-responsive matrix materials, may permit a cosmetic design to be applied using an array of color tuples, applied by modulating the photo-responsive matrix materials, to provide a difference color by subtractive mixing.

Overlying the photochromic layer 330, the photochromic formulation 300 may include an encapsulation layer 340. The encapsulation layer 340 may be or include an inert polymeric material providing an chemical and/or diffusion barrier to protect the underlying materials from chemical oxidation or other degradation reactions. Similarly, the encapsulation layer may isolate the materials making up the photochromic layer 330, the shimmer-control layer 320, and the core material 310 from body surfaces (e.g., the subject's face 102 of FIG. 1). The encapsulation layer 340 may be or include a material that is transparent to photons across UV and visible wavelengths. For example, the encapsulation layer may be or include a silicone material, such as polydimethylsiloxane (PDMS).

Figure 4A:
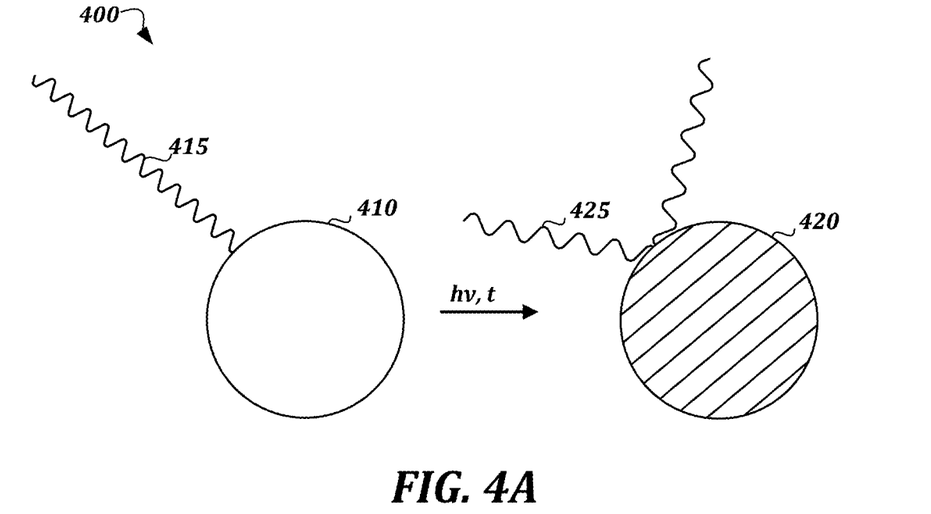
FIG. 4A is a schematic illustration of photo-modulation of the photochromic formulation of FIG. 3, in accordance with various embodiments.

FIG. 4A is a schematic illustration of photo-modulation of an example photochromic formulation 400, in accordance with various embodiments. The photochromic formulation 400 may be an example of the photochromic formulation 300 of FIG. 3, incorporating a photo-responsive pigment or dye and/or a structural color material. From an exterior perspective, a photochromic formulation 400 may be stable in a first state 410. The first state 410 may describe a first diffuse color, such as white, black, a color selected from a palette of skin tone colors (e.g., a sum color produced by additive mixing of multiple photochromic materials). Alternatively, the first state 410 may be at least partially transparent, to reduce the visual profile of the first state 410 and to blend the photochromic formulation 400 into the body surface behind.

Under irradiation by photons of one or more characteristic wavelengths 415, the photochromic formulation may transition from the first state 410 to a second state 420. The second state 420 may be characterized by a diffuse color, as when the photochromic formulation 400 includes a photonic crystal or a blend of photochromic materials. As described above, the diffuse color may result from sctructural color or subtractive color mixing, and may be characterized by wavelength-dependent reflectance of photons of one or more wavelengths 425. For photochromic materials, color rendering results from subtractive mixing of two or more photo-responsive pigments, while for structural colors, each particle may be characterized by a single diffuse color. As such, the number of wavelengths 425 corresponds to the type of material making up the photochromic formulation 400. In an illustrative example, for a structural color particle, the characteristic wavelength 415 may be in the visible spectrum, and may be applied to transition a photo-responsive material, such as spiropyran or naphthopyran, from a diffuse black color to a transparent color, thereby revealing a photonic crystal layer (e.g., either layer 330 or core material 310 of FIG. 3), which reflects the wavelength 425. Similarly, for a photochromic dye or pigment particle, the characteristic wavelength 415 may include multiple wavelengths to modulate a triad or tetrad of photo-responsive materials, resulting color rendering by subtractive mixing. As described above, in such cases, the wavelength 425 may include multiple wavelengths, received and interpreted by the human eye as a single diffuse color.

In some embodiments, the photochromic formulation 400 may be "locked in" to the second state 420. In this context, "locking in" refers to a process whereby the photochromic formulation 400 includes a photo-responsive material that isomerizes, polymerizes, or undergoes another chemical change in response to irradiation by a "locking" wavelength, different from the characteristic wavelength 415. The photo-responsive material may be an example of the encapsulation layer (e.g., encapsulation layer 340 of FIG. 3), and the change may result in the encapsulation layer absorbing the characteristic wavelength 415 and preventing further modulation of the photochromic material. In an illustrative example, where the second state 420 is stable after irradiation under the characteristic wavelength 415 in the UV range, the encapsulation layer of the photochromic formulation 400 may be photo-polymerized to become a UV-absorbing polymer, after which the photochromic formulation 400 is "locked" in the second state 420. Locking in, as such, may also apply to matrix materials.

Figure 4B:
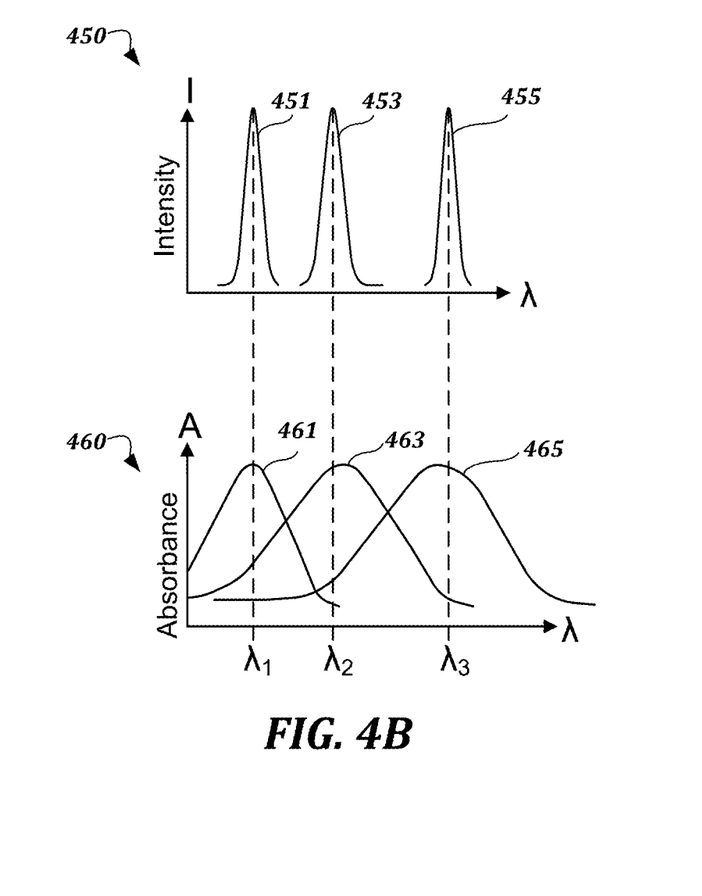
FIG. 4B describes spectroscopic aspects of the system of FIG. 1, including intensity spectra and absorbance spectra for three illumination sources and three photochromic materials, in accordance with various embodiments.

FIG. 4B describes spectroscopic aspects of the photochromic system, including intensity spectrum 450 and absorbance spectrum 460 for three illumination sources and three photochromic materials, respectively, in accordance with various embodiments. The photochromic formulation with which the cosmetic design (e.g., example cosmetic design 200 of FIG. 2) is implemented may be or include a blend of multiple photo-responsive and/or photochromic materials, as described in reference to FIG. 3 and FIG. 4B. In the example spectra illustrated, the intensity spectrum 450 represents the excitation or deactivation spectra of three different photochromic or photo-responsive materials. For example, the three materials may correspond to a CMY triad where each color channel is independently modulated by a wavelength included in intensity spectrum 450. Alternatively, the three materials may correspond to three different photo-responsive materials that each transition from transparent to opaque under irradiation by a respective wavelength in intensity spectrum 450.

Each constituent peak of the spectrum 450 may be generated by the illumination source of the system 100 described in reference to FIG. 1. For example, a first emission peak 451, corresponding to a bluish color in the visual spectrum, may be selected to correspond to a first absorbance band 461 of one of the materials. Similarly, a second emission peak 453 may be selected to correspond to a second absorbance band 463 of a second of the materials. Similarly, a third emission peak 455 may be selected to correspond to a third absorbance band 465 of a third of the materials. In this way, the illumination source (e.g., illumination source(s) 108 of FIG. 1) may be configured to expose the photochromic formulation at or near absorbance maxima of the materials, as illustrated in absorbance spectra 460. For example, the three line sources 451, 453, and 455 of the emission spectrum 450 are aligned with three central wavelengths $\lambda_{1-3}$ for independently modulating three color channels (CMY, RGB, or otherwise) as an approach to rendering a full spectrum of colors described in the cosmetic design of FIG. 2 (e.g., cosmetic design 200 of FIG. 2). In some embodiments, the three central wavelengths may within ranges of 410-475 nm, 490-540 nm, and 600-670 nm, respectively, corresponding to bluish, greenish, and reddish light. In this context, the term "central wavelength" describes a peak emission intensity around which intensity follows a distribution of emission intensity, as determined by optical properties of the illumination source that may differ for different emission modalities. For example, a coherent line-source (e.g., a laser) may emit at a characteristic central wavelength with a relatively narrow distribution on either side. By contrast, a broad-spectrum illumination source, such as a black-body source, may be characterized by a wavelength distribution that is determined by a passband of a filter used to select a given central wavelength. In this way, an illumination source may emit photons at a central wavelength within one of the ranges described above, characterized by a distribution of emission intensity at higher energy and lower energy determined by the source and optics. In some embodiments, the central wavelengths may be in the ultraviolet spectral range less than 400 nm or in the NIR or IR ranges, longer than 750 nm.

In some embodiments, the central wavelengths of the illumination source(s) are different. Even so, channel crosstalk may be observable in some cases, where emission intensity distributions for one or more wavelengths is broad enough to overlap with the nearest neighboring central wavelength. While crosstalk may impair the individual addressability of the respective photo-responsive materials, limited crosstalk may have limited to negligible impact on the color rendering fidelity, where dynamics of photochromaticism are relatively slow or where colors are typically blended. For example, a first photo-responsive pigment or dye may respond to bluish light relatively rapidly, where a second photo-responsive pigment or dye may respond to greenish light relatively slowly. As such, where the emission intensity of a bluish central wavelength may extend into the greenish range, the exposure time of the green-sensitive material to greenish illumination may be such that little to no transition is observable in the green-sensitive material. Similarly, relatively few colors exclude one or more of the triad or tetrad channels entirely. In this way, the relative impact of low-level channel overlap may be limited to a marginal change, rather than a step change in color rendering strength.

Figure 5:
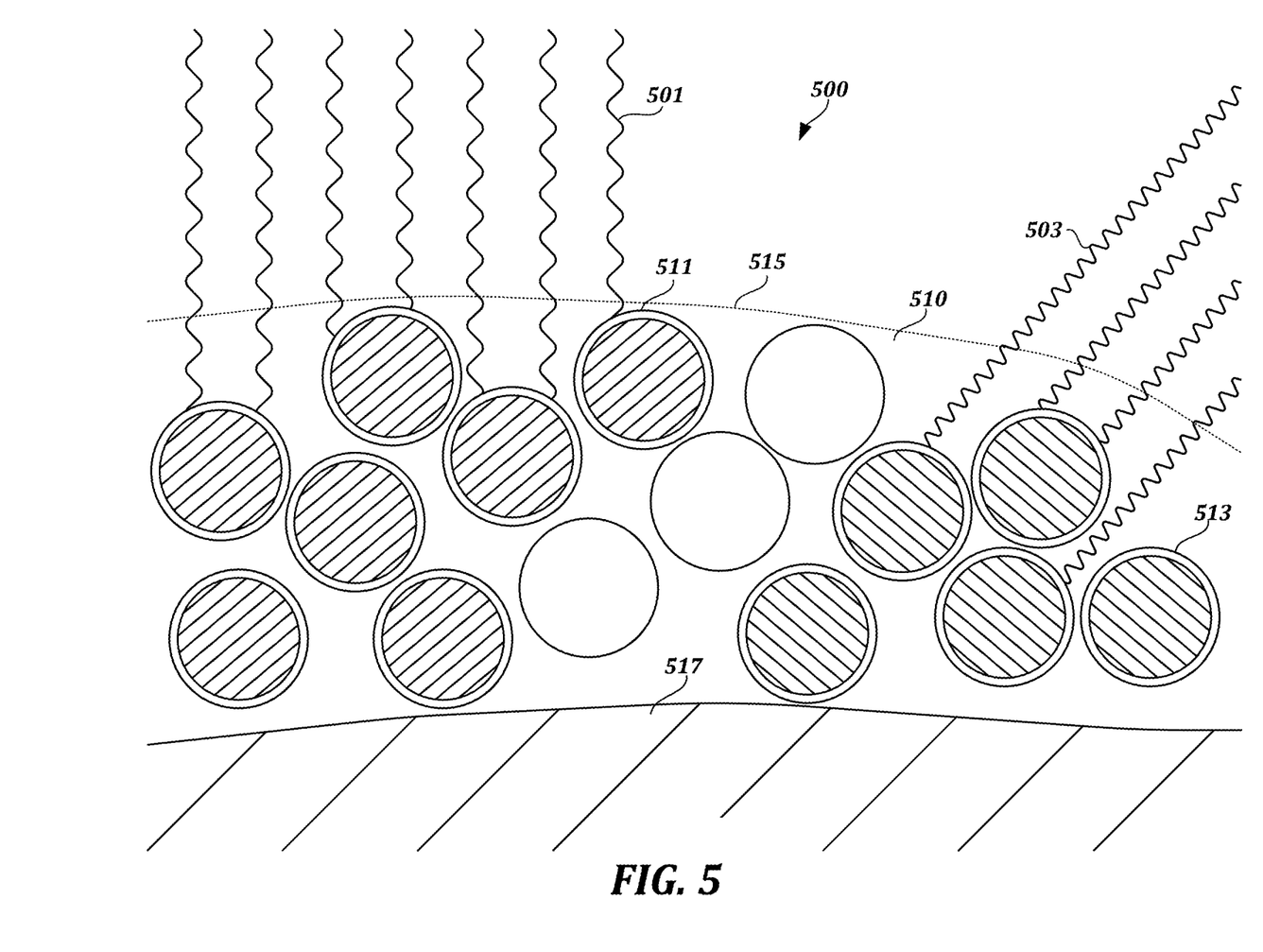
FIG. 5 is a schematic illustration of a cosmetic formulation under face-on illumination and under low-angle illumination to produce polychromatic designs, in accordance with various embodiments.

FIG. 5 is a schematic illustration of a photochromic formulation 500 under face-on illumination 501 and under low-angle illumination 503 using the system of FIG. 1 to produce polychromatic designs, in accordance with various embodiments. As illustrated, the photochromic formulation 500 includes a plurality of particulate photochromic materials 510 in various color-states as modulated by the illumination source (e.g., illumination source 108 of FIG. 1). As shown, a first subset of the photochromic materials 510, exposed to the face-on illumination 501, are expressing a first color state 511, while a second subset of the photochromic materials 510, exposed to the low-angle illumination 503, are expressing a second color state 513.

As illustrated, the photochromic formulation 500 may be or include a photo-responsive powder including a blend of photochromic materials, as described in reference to FIG. 3. Additionally or alternatively, the photochromic formulation 500 may further include a matrix material 515, such as a neutral cream or ointment that is transparent to the excitation wavelengths used to modulate the photochromic materials 510. The matrix material 515 may serve to adhere the photochromic materials 510 to the surface of the skin 517 (e.g., in region of interest 120 of FIG. 1), such that the design is preserved or does not run, for example, in response to perspiration or other physiological processes. In some embodiments, the matrix material 515 may include a dispersive material, such as a metal ceramic (e.g., titanium oxide), to absorb ultraviolet energy, such that the surface of the skin 517 may be afforded additional protection. As described in more detail in reference to FIG. 6, the face-on illumination 401 and the low-angle illumination 503 may be provided by the same illumination source by re-orienting the surface of the skin 517 relative to the illumination source. In some embodiments, the system controlling the illumination source may incorporate multiple illumination sources in multiple orientations, such that both face-on illumination 501 and low-angle illumination 503 may be provided in a single position.

Figure 6:
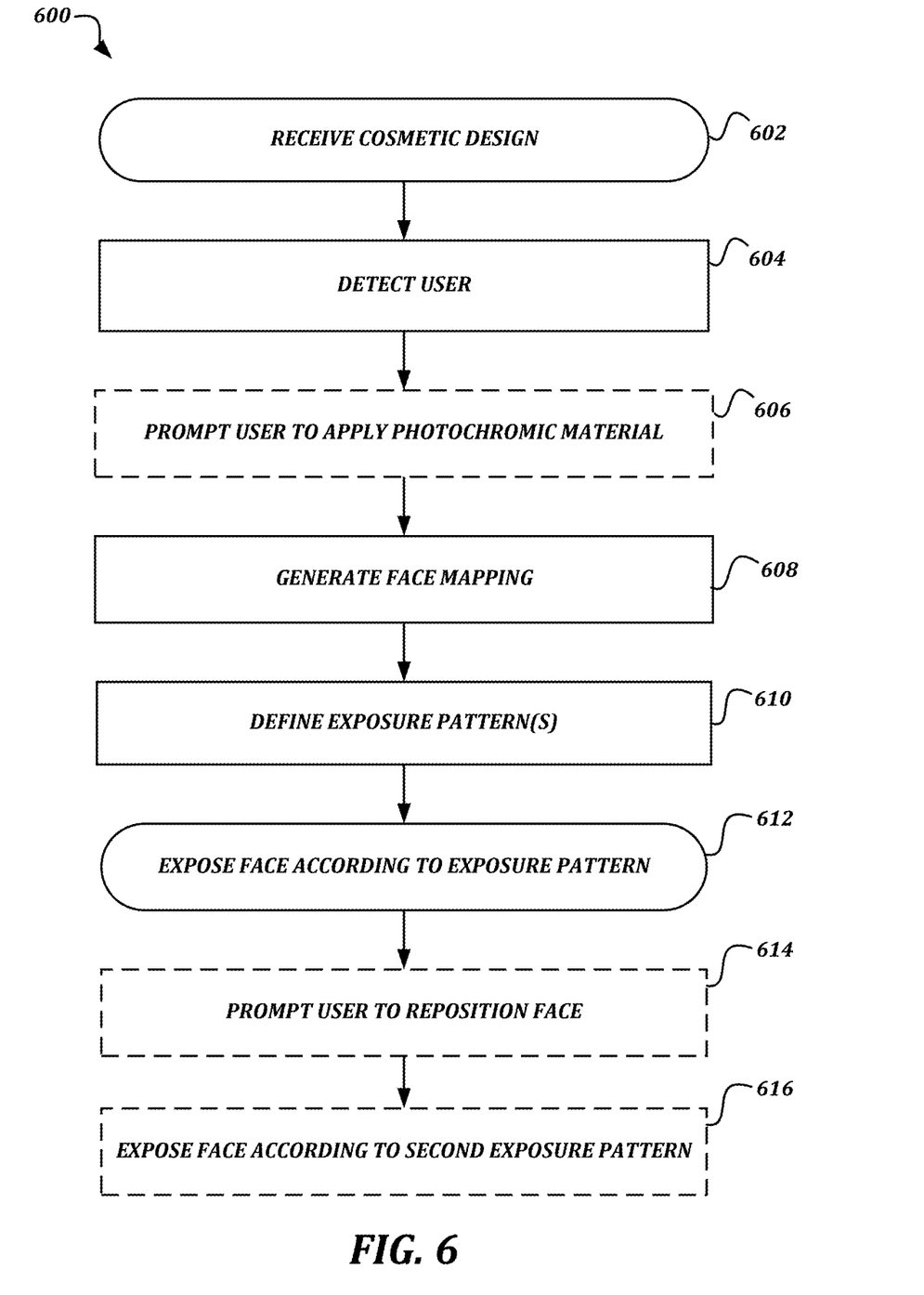
FIG. 6 is a flowchart that illustrates an example method for applying a cosmetic design using the photochromic material of FIG. 3, in accordance with various embodiments.

FIG. 6 is a flowchart that illustrates an example method for applying a cosmetic design using the photochromic material of FIG. 3, in accordance with various embodiments. The example method 600 may be performed by a computer system including one or more computing devices, such as client computing device 104 of FIG. 1. The example method 600 may be stored as computer-executable instructions on a computer-readable memory device. In this way, the computer system may implement the operations of example method 600 as part of executing the instructions.

At operation 602, the computer system receives a numerical representation of a cosmetic design. The numerical representation of the cosmetic design includes a tensor of color intensity information for a plurality of colors. The plurality of colors correspond to a cosmetic composition (e.g., photochromic formulation 500 of FIG. 5) including a mixture of photochromic materials. The computer system may receive the numerical representation of the cosmetic design (e.g., cosmetic design 200 of FIG. 2) from a user through a user interface of the computer system or through a personal electronic device. The numerical representation of the cosmetic design may be associated with a unique design identifier and may be retrieved from a data store, such that the tensor of color intensity information may be requested and/or retrieved by computer system in response to receiving a the unique design identifier.

At operation 604, the computer system detects, using a camera in electronic communication with the computer system, a user of the system facing a visible light mirror (e.g., mirror 106 of FIG. 1). In some embodiments, the camera is in optical communication with the visible light mirror via a partially transparent portion of the visible light mirror (e.g., first portion 112-1 of FIG. 1). In this context, detecting the user may include multiple operations included as part of face-detection and recognition routines. For example, the computer system may store feature data for a number of faces, such that the computer system is able to detect and identify the face present in the field of view of the camera (e.g., field of view 152 of FIG. 1). Such identification may benefit the system by reducing the resource demand associated with generating face mappings and projections. For example, by storing depth and image data, the computer system may rely on periodic re-initialization for the 3D mapping operations, rather than continuous mapping, which may be more computationally intensive.

The method 600 may optionally include generating, by the computer system, a prompt for the user to apply the mixture of photochromic materials at operation 606. As described in reference to FIG. 1, prompting the user to apply the photochromic formulation (e.g., photochromic formulation 500 of FIG. 5) may serve as one of a number of visual/auditory guides or prompts provided to the user. Such prompts may facilitate the application of cosmetic designs, for example, where the client computing device is not equipped with a sensor to detect the presence of the photochromic formulation. In some embodiments, the photochromic formulation includes a constituent compound or that is detectable optically. For example, a matrix (e.g., matrix material 515 of FIG. 5) may include a material that absorbs a characteristic wavelength for which the computer system is provided with a source that is typically reflected by human skin. Additionally and/or alternatively, the matrix may include a material that reflects or fluoresces under a characteristic wavelength of illumination. In this way, the optional operation 606 may be triggered in response to the computer system determining that the user has not applied the photochromic formulation.

At operation 608, the computer system generates, using the camera, a numerical representation of a portion of a face of the user (e.g., region of interest 120 of subject's face 102 of FIG. 1). The numerical representation of the face includes a tensor of position information defining a surface of the face. The tensor of position information is described in other terms as a face-mapping or a 3D mapping of the face of the user. The computer system may implement various techniques to collect and generate depth data describing the surface to which the cosmetic design will be applied. For example, the computer system may incorporate or be electronically coupled with sensors including, but not limited to, time-of-flight cameras, stereoscopic cameras, LiDAR sensors, or point-tracking systems, to generate the numerical representation of the face. As described in more detail in reference to FIG. 1 the numerical representation of the face may be stored in memory of the computer system and/or in separate data store for use in generating projections of the cosmetic design onto the face mapping.

At operation 610, the computer system defines one or more exposure patterns for the surface of the face, at least in part by projecting the tensor of color intensity information onto the tensor of position information. As described in more detail in reference to FIGS. 2-4, the exposure patterns may include data for a set of characteristic wavelengths generated by the sources incorporated or in electronic communication with the computer system. For example, an exposure pattern may include spatially localized emission levels and durations for each of a map of polygons (e.g., polygons 212 of FIG. 2B) corresponding to a position on the face. In this way, the computer system may generate an exposure sequence, in terms of drive instructions for the sources, to apply the cosmetic design to the specific face of the user.

At operation 612, using an illumination source (e.g., illumination source 108 of FIG. 1) in electronic communication with the computer system, the computer system exposes a portion of the user's skin (e.g., region of interest 120 of FIG. 1) with a plurality of discrete wavelength channels. The exposure is effected in accordance with the exposure pattern. In some embodiments, the illumination source is physically coupled with the visible light mirror and configured to emit the plurality of discrete wavelength channels. In some embodiments, the illumination source is optically coupled with the mirror via a unidirectional transparent portion (e.g., second portion 112-2 of FIG. 1), such that the illumination source emits the plurality of discrete wavelength channels through the mirror via the unidirectional transparent portion. The sources can be steered by the computer system as part of processing the exposure pattern into drive instructions for the sources. For example, the sources may include beam steering optics that rely on electronic actuation or dynamic lensing/optics to direct the source beam toward a specific position on the face. In some embodiments, the sources are configured to emit a field of light covering the entire surface, but with variable wavelength content at each of a number of pixels, reproducing the projected design, as described in more detail in reference to FIG. 2B. In such cases, the sources may include dynamic filters, such as programmable diffraction grating arrays or programmable filter arrays. Operation 612 may optionally include locking in the design by an additional exposure with a lock wavelength, as described in reference to FIG. 4A.

The method 600 may optionally include operation 614, whereby the computer system generates a second prompt for the user to reposition relative to the cameras (e.g., reposition from a face-on posture to a semi-profile posture), such that the illumination sources may be aligned with a different portion of the face. As described in more detail in reference to FIG. 5, multiple angles of exposure may impart to the photochromic formulation an angular-color effect, such as iridescence, that is not typically available using pigment-based cosmetics. Subsequent operation 614, the method 600 may optionally include operation 616, whereby the computer system exposes the user's face according to a second exposure pattern. The second exposure pattern may include low-angle illumination, as part of applying angular or layered color to the first portion of the user's face exposed at operation 612. Similarly, operation 616 may include face-on illumination of a second portion of the user's face, such that a different region may express a color pattern according to the cosmetic design received at operation 602.

Figure 7:
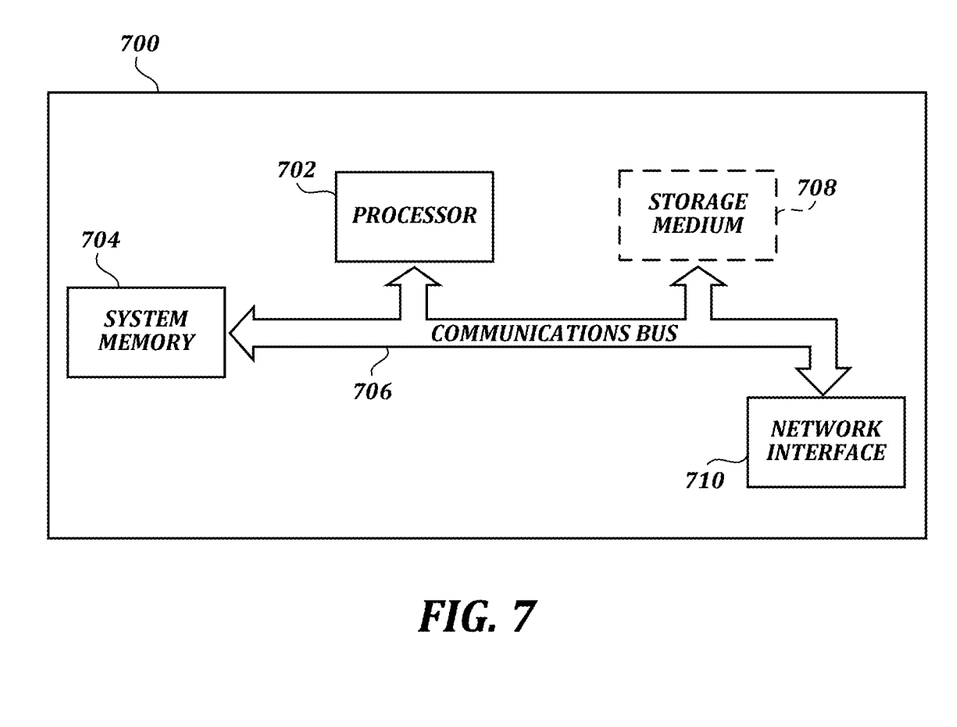
FIG. 7 is a block diagram that illustrates aspects of an illustrative computing device appropriate for use as a computing device of the present disclosure.

FIG. 7 is a block diagram that illustrates aspects of an example computing device 700, in accordance with various embodiments. While multiple different types of computing devices were discussed above, the exemplary computing device 700 describes various elements that are common to many different types of computing devices. While FIG. 7 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 700 may be any one of any number of currently available or yet to be developed devices.

In its most basic configuration, the computing device 700 includes at least one processor 702 and a system memory 704 connected by a communication bus 706. Depending on the exact configuration and type of device, the system memory 704 may be volatile or nonvolatile memory, such as read only memory ("ROM"), random access memory ("RAM"), EEPROM, flash memory, or similar memory technology. Those of ordinary skill in the art and others will recognize that system memory 704 typically stores data and/or program modules that are immediately accessible to and/or currently being operated on by the processor 702. In this regard, the processor 702 may serve as a computational center of the computing device 700 by supporting the execution of instructions.

As further illustrated in FIG. 7, the computing device 700 may include a network interface 710 comprising one or more components for communicating with other devices over a network. Embodiments of the present disclosure may access basic services that utilize the network interface 710 to perform communications using common network protocols. The network interface 710 may also include a wireless network interface configured to communicate via one or more wireless communication protocols, such as WiFi, 2G, 3G, LTE, WiMAX, Bluetooth, Bluetooth low energy, and/or the like. As will be appreciated by one of ordinary skill in the art, the network interface 710 illustrated in FIG. 7 may represent one or more wireless interfaces or physical communication interfaces described and illustrated above with respect to particular components of the system 100.

In the exemplary embodiment depicted in FIG. 7, the computing device 700 also includes a storage medium 708. However, services may be accessed using a computing device that does not include means for persisting data to a local storage medium. Therefore, the storage medium 708 depicted in FIG. 7 is represented with a dashed line to indicate that the storage medium 708 is optional. In any event, the storage medium 708 may be volatile or nonvolatile, removable or nonremovable, implemented using any technology capable of storing information including, but not limited to, a hard disk drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 704 and storage medium 708 depicted in FIG. 7 are merely examples of computer-readable media.

Suitable implementations of computing devices that include a processor 702, system memory 704, communication bus 706, storage medium 708, and network interface 710 are known and commercially available. For ease of illustration and because it is not important for an understanding of the claimed subject matter, FIG. 7 does not show some of the typical components of many computing devices. In this regard, the computing device 700 may include input devices, such as a keyboard, keypad, mouse, microphone, touch input device, touch screen, and/or the like. Such input devices may be coupled to the computing device 700 by wired or wireless connections including RF, infrared, serial, parallel, Bluetooth, Bluetooth low energy, USB, or other suitable connections protocols using wireless or physical connections. Similarly, the computing device 700 may also include output devices such as a display, speakers, printer, etc. Since these devices are well known in the art, they are not illustrated or described further herein.

While illustrative embodiments have been illustrated and described, it will be appreciated that various changes can be made therein without departing from the spirit and scope of the devices, methods, and systems described.

The invention claimed is:

1. A photochromic formulation, comprising:
   a core material; and
   a photochromic layer or structural color layer overlying the core material and forming a particle centered around the core material;
   wherein the photochromic layer or structural color layer includes porous clusters suspended in a photo-responsive matrix;
   wherein the photochromic layer includes a photo-responsive material in which the photo-responsive material absorbs light at a characteristic wavelength; and
   wherein the photo-responsive material undergoes a chemical change to lock in a second state, that is UV absorbing, in response to irradiation by a locking wavelength that is different from the characteristic wavelength.

2. The photochromic formulation of claim 1, wherein the photochromic layer comprises a plurality of photochromic materials, including:
   a first photo-responsive pigment characterized by reversible diffuse reflectance at a first central wavelength from 490 nm to 520 nm in response to irradiation by photons of a first characteristic wavelength;
   a second photo-responsive pigment characterized by reversible diffuse reflectance at a second central wavelength from 570 nm to 590 nm in response to irradiation by photons of a second characteristic wavelength; and
   a third photo-responsive pigment characterized by reversible diffuse reflectance at a third central wavelength from 450 nm to 495 nm and a fourth central wavelength from 625 nm to 740 nm in response to irradiation by photons of a third characteristic wavelength;

wherein the first characteristic wavelength, the second characteristic wavelength, and the third characteristic wavelength are different.

3. The photochromic formulation of claim 2, wherein:
the first photo-responsive pigment comprises 1,2-bis(2-methyl-5-phenyl-3-thienyl)-3,3,4,4,5,5-hexafluorocyclopentene;
the second photo-responsive pigment comprises 1,2-bis(2-methyl-5-phenyl-3-thienyl)-3,3,4,4,5,5-hexafluorocyclopentene; and
the third photo-responsive pigment comprises 1,2-bis(3-methylbenzo (b) thiophen-2-yl) perfluorocyclopentene.

4. The photochromic formulation of claim 1, wherein the photochromic layer comprises spiropyrans, spirooxazines, diarylethenes, azobenzenes, quinones, silver halides, or zinc halides.

5. The photochromic formulation of claim 1, wherein the core material comprises a reflective mineral.

6. The photochromic formulation of claim 5, wherein the reflective mineral comprises mica, titanium oxide, or silicon oxide.

7. The photochromic formulation of claim 5, further comprising:
a shimmer-control layer, interposed between the core material and the photochromic layer, wherein the shimmer-control layer includes a photo-responsive material characterized by a transition from visible transparency to visible opacity when exposed to irradiation of a characteristic wavelength, the visible opacity corresponding to broad reflectance in the visible spectrum.

8. The photochromic formulation of claim 7, wherein the transition from visible transparency to visible opacity is progressive in proportion to an extent of the irradiation.

9. The photochromic formulation of claim 1, wherein the particle is characterized by a diameter less than or equal to 20 micrometers.

10. The photochromic formulation of claim 1, wherein the photochromic layer or structural color layer comprises a photonic crystal material, comprising:
a first photonic crystal material characterized by a first structural color in the blueish range;
a second photonic crystal material characterized by a second structural color in the greenish range; or
a third photonic crystal material characterized by a third structural color in the reddish range.

11. The photochromic formulation of claim 10, further comprising a plurality of particles including the particle, wherein the plurality of particles includes:
a first proportion of particles comprising the first nanostructured material;
a second proportion of particles comprising the second nanostructured material; and
a third proportion of particles comprising the third nanostructured material.

12. The photochromic formulation of claim 11, wherein the first proportion, the second proportion, and the third proportion are substantially equal.

13. The photochromic formulation of claim 10, wherein:
the photochromic layer or structural color layer further comprises a photo-responsive matrix characterized by a transition from visible transparency to visible opacity when exposed to irradiation of a characteristic wavelength associated with the respective structural color; and
the nanostructured material comprises a plurality of porous clusters suspended in the photo-responsive matrix.

14. The photochromic formulation of claim 13, wherein the porous clusters comprise inverse opal formed from silicon oxide or titanium oxide.

15. The photochromic formulation of claim 10, further comprising:
a brightness layer overlying the photochromic layer, wherein the brightness layer includes a photo-responsive material characterized by a transition from visible transparency to visible opacity when exposed to irradiation of a characteristic wavelength, the visible opacity corresponding to broad absorptance in the visible spectrum.

16. The photochromic formulation of claim 15, wherein the transition from visible transparency to visible opacity is progressive in proportion to an extent of the irradiation.

17. The photochromic formulation of claim 15, wherein the brightness layer comprises spiropyran or naphthopyran.

18. The photochromic formulation of claim 10, wherein the core material and the structural color material are the same material.

* * * * *